United States Patent [19]

Andres et al.

[11] Patent Number: 5,637,737
[45] Date of Patent: Jun. 10, 1997

[54] PROCESS FOR THE PREPARATION OF 2,2-DIFLUOROBENZO[1.3]DIOXOLECARBALDEHYDES

[75] Inventors: Peter Andres, Leichlingen; Albrecht Marhold, Leverkusen, both of Germany

[73] Assignee: Bayer Aktiengesellschaft, Leverkusen, Germany

[21] Appl. No.: 696,670

[22] Filed: Aug. 14, 1996

[30] Foreign Application Priority Data

Aug. 21, 1995 [DE] Germany ............ 195 30 637.6

[51] Int. Cl.$^6$ ............................................. C07D 317/46
[52] U.S. Cl. ............................................. 549/434; 549/436
[58] Field of Search ............................. 549/434, 436

[56] References Cited

U.S. PATENT DOCUMENTS

| | | | |
|---|---|---|---|
| 4,886,816 | 12/1989 | Franckowiak et al. | 514/338 |
| 5,194,628 | 3/1993 | Ackermann et al. | 548/526 |
| 5,344,944 | 9/1994 | Franckowiak et al. | 549/436 |
| 5,420,308 | 5/1995 | Andres et al. | 549/436 |
| 5,525,739 | 6/1996 | Andres et al. | 549/434 |

FOREIGN PATENT DOCUMENTS

| | | |
|---|---|---|
| 0 291 799 A2 | 11/1988 | European Pat. Off. . |
| 0 333 658 A2 | 9/1989 | European Pat. Off. . |
| 4133155 | 4/1993 | Germany . |
| 676 119 A5 | 12/1990 | Switzerland . |

OTHER PUBLICATIONS

Houben–Weyl (Methoden Der Organischen Chemie), Band VII Teil 1, Georg Thieme Verlag–Stuttgart, pp 210–217 (1954).

*Primary Examiner*—Johann Richter
*Assistant Examiner*—Laura R. Cross
*Attorney, Agent, or Firm*—Sprung Horn Kramer & Woods

[57] ABSTRACT

2,2-Difluorobenzo[1.3]dioxole-carbaldehydes are prepared in a particularly advantageous manner if methylbenzo[1.3]dioxoles are chlorinated, the resulting dichloromethyl-2,2-dichlorobenzo[1.3]dioxole is fluorinated with hydrogen fluoride and the dichloromethyl-2,2-difluorobenzo[1.3]dioxole obtained by this procedure is reacted with a carboxylic acid.

8 Claims, No Drawings

PROCESS FOR THE PREPARATION OF 2,2-DIFLUOROBENZO[1.3]DIOXOLECARBALDEHYDES

The present invention relates to a particularly advantageous process for the preparation of 2,2-difluorobenzo[1.3]dioxolecarbaldehydes from methylbenzo[1.3]dioxoles.

2,2-Difluorobenzo[1.3]dioxolecarbaldehydes are known intermediate products for plant protection agents and pharmaceutical active compounds (cf. EP-A 634 413, EP-A 606 843, DE-A 4 029 444, EP-A 333 658, U.S. Pat. No. 5,344,944 and EP-A 291 799).

3 processes are known to date for the preparation of 2,2-difluorobenzo[1.3]dioxolecarbaldehydes, and are illustrated here by the example of the preparation of 2,2-difluorobenzo[1.3]dioxole-4-carbaldehyde.

Process 1 (cf. EP-A 291 799 and U.S. Pat. No. 5,344,944):

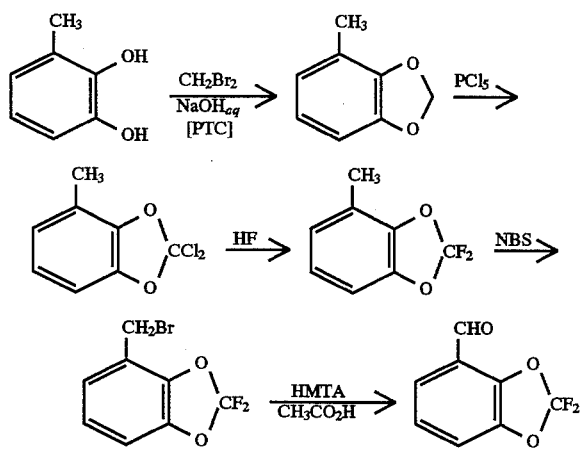

PTC denotes phase transfer catalyst, NBS denotes N-bromosuccinimide, HMTA denotes hexamethylenetetramine (=urotropin).

Process 2 (cf. EP-A 333 658):

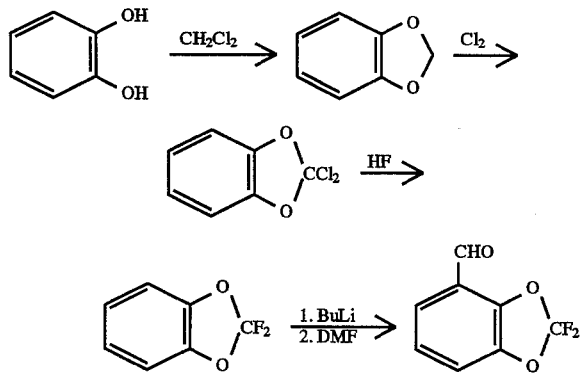

BuLi denotes butyllithium, DMF denotes dimethylformamide.

EP-A 333 658 only relates to the last process stage. The process stages to be carried out beforehand are given for ease of comparison.

Process 3 (cf. DE-A 4 133 155):

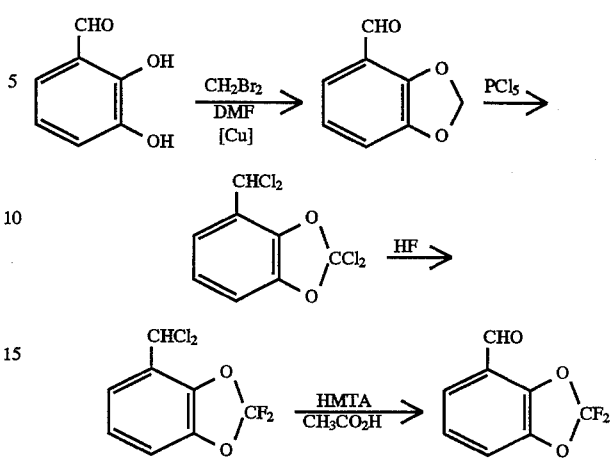

DMF denotes dimethylformamide, HMTA denotes hexamethylenetetramine.

DE-A 4 133 155 only relates to the process after the reaction of benzo[1.3]dioxo-4-carbaldehyde with phosphorus pentachloride. The process stage to be carried out beforehand is given for ease of comparison.

2,2-Difluorobenzo[1.3]dioxo-5-carbaldehyde can also be prepared by processes 1 and 3. Process 2 is limited to the preparation of the 4-carbaldehyde.

Disadvantages of the known processes are that they comprise 4 or 5 stages, are not always satisfactory in respect of the yield which can be achieved and in some cases require expensive chemicals that are poorly accessible and difficult to handle, and that relatively large amounts of residues to be disposed of are obtained.

A process has now been found for the preparation of 2,2-difluorobenzo[1.3]dioxolecarbaldehydes of the formula (I)

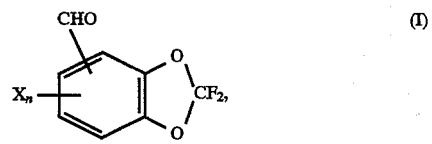

wherein

X represents fluorine and/or chlorine and n represents zero or an integer from 1 to 3, which is characterized in that methylbenzo[1.3]dioxoles of the formula

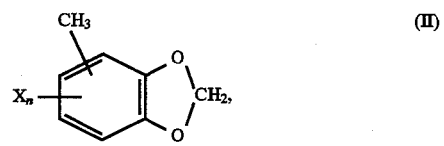

wherein X and n have the meaning given in the case of formula (I), are chlorinated, the resulting dichloromethyl-2,2-dichlorobenzo[1.3]dioxole is fluorinated with hydrogen fluoride and the dichloromethyl-2,2-difluorobenzo[1.3]dioxole obtained by this procedure is reacted with a carboxylic acid.

The process according to the invention can be illustrated by the following equation:

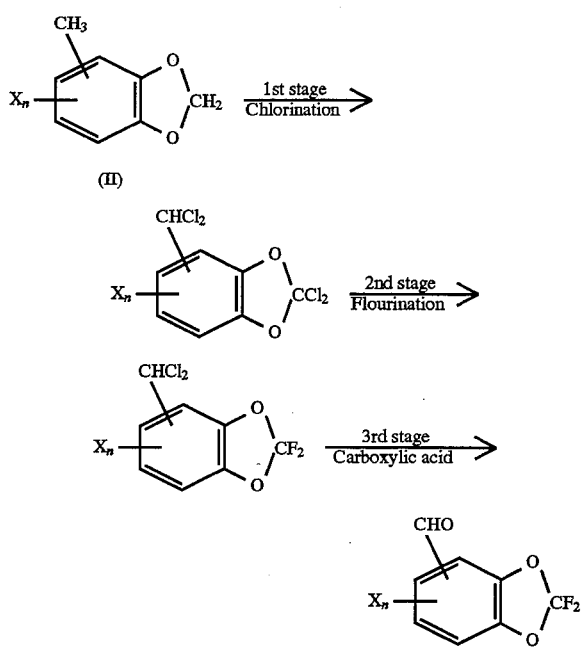

4-Methyl- or 5-methyl-benzo[1.3]-dioxoles which are optionally fluorinated on the nucleus and/or optionally chlorinated on the nucleus can be used as starting substances to prepare corresponding 2,2-difluorobenzo[1.3]dioxole-4- or -5-carbaldehydes.

Possible chlorinating agents for the chlorination in the 1st stage are, for example, chlorine, phosphorus chlorides, such as $PCl_3$ and $PCl_5$, sulphuryl chloride and mixtures thereof. Chlorine is preferred. The chlorinating agent can be employed, for example, in amounts of more than 3.5 chlorination equivalents per mole of methylbenzo[1.3]dioxole of the formula (II). This ratio is preferably 4:1 to 10:1, in particular 4.1:1 to 4.5:1.

The chlorination temperature can be, for example, in the range from 0° to 230° C. If the reaction is carried out without the addition of free radical initiators and in the absence of UV light, temperatures from 60° to 210° C., in particular 80° to 180° C., are preferred. The reaction is preferably carried out with the addition of free radical initiators or in the presence of UV light. Temperatures from 40° to 180° C., in particular 50° to 160° C., are then preferred. Possible free radical initiators are, for example: organic peroxides, such as dibenzoyl peroxide (DBPO) and aliphatic azo compounds, such as $\alpha,\alpha'$-azoisobutyronitrile (AIBN).

Free radical initiators can be added, for example, in amounts of 0.1 to 10 mol %. It is furthermore preferable to start the chlorination at a relatively lower temperature, for example at 40° to 100° C., and to bring it to completion at a relatively higher temperature, for example at 120° to 180° C. The chlorination can be carried out in the presence of a solvent, for example in the presence of a perchlorinated hydrocarbon or of a halogenated aromatic, such as chlorobenzene or chlorobenzotrifluoride. The reaction is preferably carried out without addition of a solvent.

The chlorination is preferably carried out by initially introducing the precursor into the reaction vessel and metering in the chlorinating agent.

After the chlorination, a mixture is present which in general comprises, in addition to the desired dichloromethyl-2,2-dichlorobenzo[1.3]dioxole, the corresponding methyl compound, the corresponding monochloromethyl compound and the corresponding trichloromethyl compound in smaller amounts. This mixture can be separated by distillation, preferably under reduced pressure. The hypochlorinated constituents of the mixture can be recycled into the chlorination.

At least 2 mol of hydrogen fluoride per mole of the particular dichloromethyl-2,2-dichlorobenzo[1.3]dioxole, for example, can be employed in the fluorination of the 2nd stage. This amount is preferably 2 to 40 mol, in particular 5 to 30 mol. The temperature can be, for example, in the range from −35° to +180° C. −25° to +40° C., in particular −20° to +15° C., are preferred. The fluorination can be carried out in the presence of a solvent, for example in the presence of inert aliphatic or aromatic solvents, such as methylene chloride and nitrobenzene. The reaction is preferably carried out without addition of a solvent. The sequence of the addition of the reactants is not of particular importance. At temperatures above 0° C., the precursor is preferably to be introduced into the reaction vessel and hydrogen fluoride metered in.

The mixture present after the fluorination can be worked up, for example, by first removing most of the excess hydrogen fluoride, for example by stripping in vacuo, pouring the residue which remains onto ice-water and separating off, drying and distilling the organic phase. A dichloromethyl-2,2-difluorobenzo[1.3]dioxole which is suitable for carrying out the 3rd stage is thus obtained.

The most diverse carboxylic acids are possible for the reaction with a carboxylic acid. The carboxylic acids can be saturated or unsaturated, for example aromatic, they can be mono- or polybasic, and they can optionally contain substituents, for example one or more halogen, nitro, carbonyl, alkoxycarbonyl, hydroxyl and/or cyano substituents. Straight-chain and branched 1- to 3-basic $C_1$-$C_{10}$-alkyl- and 1- to 3-basic $C_6$-$C_{12}$-aryl-carboxylic acids, which can optionally contain 1 to 3 of the abovementioned substituents, are preferred. Individual examples which may be mentioned are: formic acid, acetic acid, propionic acid, butyric acids, valeric acids, trimethylacetic acid, fluoro-, difluoro- and trifluoroacetic acid, chloro-, dichloro- and trichloroacetic acid, chloropropionic acid ($\alpha$ and $\beta$), glycolic acid, lactic acid, cyanoacetic acid, oxalic acid, succinic acid, malonic acid, maleic acid, fumaric acid, benzoic acid, polyol acids, chlorobenzoic acids, nitrobenzoic acids, hydroxybenzoic acids, phthalic acid, isophthalic acid and terephthalic acid.

Formic and oxalic acid are particularly preferred, especially formic acid. It is also possible to employ mixtures of 2 or more carboxylic acids. The acids may contain water, but are preferably anhydrous.

The molar ratio of the carboxylic acids to the particular dichloromethyl-2,2-difluorobenzo[1.3]dioxole can be, for example, in the range from 1:1 to 50:1. This ratio is preferably 5:1 to 30:1, in particular 10:1 to 25:1. This reaction can optionally be carried out in the presence of water and/or catalysts. Possible catalysts are, for example, metal chlorides, such as aluminium(III), boron(III), iron (III), titanium(IV) and zinc(II) chlorides, in amounts of up to 10 mol %, based on the precursor. The reaction is preferably carried out without a catalyst. The reaction can be carried out, for example, at temperatures in the range from 0° to 150° C. Temperatures in the range from 20° to 130° C., in particular 50° to 110° C., are preferred. The reactants can be added in any desired sequence. If the reaction is carried out at elevated temperature, the reactants can also first be brought together and then brought to the reaction temperature. If formic acid has been used, the mixture present after the reaction can be worked up, for example, by distillation, preferably under reduced pressure, during which excess formic acid is initially separated off, and then the particular 2,2-difluorobenzo[1.3]-dioxole-carbaldehyde prepared. If oxalic acid has been used, the reaction mixture can be poured onto water and the product obtained by distillation from the organic phase which forms. An analogous procedure can be followed if other acids are used.

The process according to the invention has a number of advantages: thus, it has 1 to 2 reaction stages fewer than known processes. It is particularly surprising here that two very different parts of the molecule, that is to say the methylene group in the methylenedioxy bridge and the methyl group on the phenyl ring, can be chlorinated in the 1st stage of the process according to the invention. In respect of yield, chemicals employed and residues to be disposed of, the reaction of a dichloromethyl-2,2-difluorobenzo[1.3]dioxole with carboxylic acid is considerably more advantageous than the known reaction with hexamethylenetetramine/acetic acid. The difficult handling of butyllithium is not necessary. It is also surprising that the chlorination to be carried out according to the invention can be undertaken with elemental chlorine, since, for corresponding chlorinations of the prior art, only phosphorus pentachloride is mentioned as a chlorinating agent (see processes 1 and 3 described above).

EXAMPLES

Percentage data given below are percentage by weight, unless noted otherwise.

EXAMPLE 1

(Preparation of the starting substance 4-methylbenzo[1.3]dioxole—not according to the invention)

A mixture of 124 g of 3-methylpyrocatechol, 255 g of methylene chloride, 233 g of sodium carbonate and 1000 ml of dimethylsulphoxide was stirred at 115° C. for 22 hours. All the volatile constituents were then distilled off in vacuo under about 2 mbar at 120° to 140° C. and the distillate was poured onto 1000 ml of water. The organic phase which forms was separated off and the aqueous phase was extracted with methyl tert-butyl ether. The combined organic phases were washed with water, dried and concentrated. 104.2 g (74.9% of theory) of 4-methylbenzo[1.3]dioxole with a purity, determined by gas chromatography, of 97.8% were thus obtained.

When potassium carbonate was used instead of sodium carbonate, it was possible to increase the yield to virtually 90% of theory.

EXAMPLE 2

(Preparation of 4-dichloromethyl-2,2-dichlorobenzo[1.3]dioxole)

102 g of 4-methylbenzo[1.3]dioxole and 0.5 g of AIBN were initially introduced into the reaction vessel and the mixture was heated to 70° C., while stirring. 114 g of chlorine were then passed in over a period of 6 hours. The oil bath temperature was now increased to 150° C. and a further 114 g of chlorine were passed in over a period of 18 hours. The mixture was then allowed to cool to room temperature. The 188 g of the crude product mixture thus obtained had the following composition:

4% of 4-methyl-2,2-dichlorobenzo[1.3]dioxole,

28% of 4-chloromethyl-2,2-dichlorobenzo[1.3]dioxole,

49% of 4-dichloromethyl-2,2-dichlorobenzo[1.3]dioxole and

5% of 4-trichloromethyl-2,2-dichlorobenzo[1.3]dioxole.

This product mixture was separated by distillation over a column. During this operation, the 4-dichloromethyl-2,2-dichlorobenzo[1.3]dioxole passed over at a boiling point of 99° to 103° C. under 0.35 to 0.45 mbar. The 4-methyl- and the 4-chloromethyl-2,2-dichlorobenzo[1.3]dioxole were likewise isolated and recycled into the next batch of the chlorination.

EXAMPLE 3

(Preparation of 4-dichloromethyl-2,2-difluorobenzo[1.3]dioxole)

49.5 g of 4-dichloromethyl-2,2-dichlorobenzo[1.3]dioxole were added dropwise at −15° C. to 72 g of anhydrous hydrogen fluoride and the mixture was subsequently stirred at −15° C. for 3 hours. Most of the hydrogen fluoride was then stripped off in vacuo under 50 mbar. After separation of the phases, the organic phase was shaken with ice-water, separated off, dried and distilled. 43.3 g (97.5% of theory) of 4-dichloromethyl-2,2-difluorobenzo[1.3]dioxole, having a purity, determined by gas chromatography, of 97.7% and a boiling point of 97° to 99° C. under 22 mbar, were obtained.

EXAMPLE 4

(Preparation of 2,2-difluorobenzo[1.3]dioxole-4-carbaldehyde)

A mixture of 48.2 g of 97.3% pure 4-dichloromethyl-2,2-difluorobenzo[1.3]dioxole and 230 g of formic acid was heated to 100° C. and stirred at this temperature for 6 hours. Excess formic acid was subsequently first distilled off in vacuo, and 28.6 g (=78.1% of theory) of 2,2-difluorobenzo[1.3]dioxole-4-carbaldehyde having a boiling point of 70° to 73° C. under 2.3 mbar and a purity, determined by gas chromatography, of 98.8% were then collected.

What is claimed is:

1. A process for the preparation of a 2,2-difluorobenzo[1.3]dioxolecarbaldehyde of the formula (I)

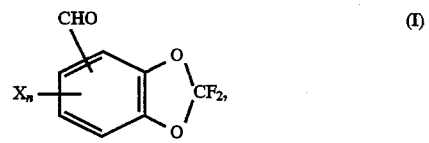

wherein

X is selected from fluorine and chlorine and n represents zero or an integer from 1 to 3, in which a methylbenzo[1.3]dioxole of the formula

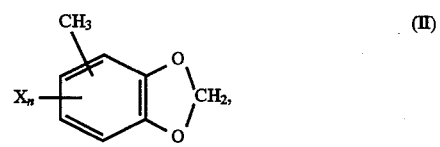

wherein X and n have the meaning given in the case of formula (I), are chlorinated, the resulting dichloromethyl-2,2-dichlorobenzo[1.3]dioxole is fluorinated with hydrogen fluoride and the dichloromethyl-2,2-difluorobenzo[1.3]dioxole obtained by this procedure is reacted with a carboxylic acid.

2. The process of claim 1, in which chlorine, phosphorus chlorides, sulphuryl chloride or mixtures thereof in amounts of more than 3.5 chlorination equivalents per mole of methylbenzo[1.3]dioxole of the formula (II) are employed as the chlorinating agent and the chlorination is carried out at temperatures in the range from 0° to 230° C.

3. The process of claim 1, in which the chlorination is carried out without the addition of free radical initiators and in the absence of UV light and at temperatures from 60° to 210° C.

4. The process of claim 1, in which the chlorination is carried out with the addition of free radical initiators or in the presence of UV light and at temperatures from 40° to 180° C.

5. The process of claim 1 in which the chlorination is started at temperatures from 40° to 100° C. and brought to completion at temperatures from 120° to 180° C.

6. The process of claim 1, in which at least 2 mol of hydrogen fluoride per mole of dichloromethyl-2,2-dichlorobenzo[1.3]dioxole are employed in the fluorination and the fluorination is carried out at temperatures in the range from −35° to +180° C.

7. The process of claim 1, in which 1:1 to 50:1 moles of the acid per mole of dichloromethyl-2,2-difluorobenzo[1.3]dioxole are employed in the reaction with a carboxylic acid.

8. The process of claim 1, in which the reaction is carried out with one or both of formic and oxalic acid at temperatures in the range from 0° to 150° C.

* * * * *